United States Patent
Aguirre

(10) Patent No.: US 11,346,820 B2
(45) Date of Patent: May 31, 2022

(54) HPLC-PDA METHOD AND USES THEREOF IN PHYTOESTROGEN MEASUREMENT

(71) Applicant: The Board Of Regents, The University of Texas System, Austin, TX (US)

(72) Inventor: Maria Teresa Aguirre, San Benito, TX (US)

(73) Assignee: The Board of Regents of The University of Texas System, Austin, TX (US)

( * ) Notice: Subject to any disclaimer, the term of this patent is extended or adjusted under 35 U.S.C. 154(b) by 205 days.

(21) Appl. No.: 16/721,075

(22) Filed: Dec. 19, 2019

(65) Prior Publication Data

US 2020/0225196 A1     Jul. 16, 2020

Related U.S. Application Data

(60) Provisional application No. 62/792,180, filed on Jan. 14, 2019.

(51) Int. Cl.

| | |
|---|---|
| *G01N 30/06* | (2006.01) |
| *G01N 30/74* | (2006.01) |
| *G01N 30/86* | (2006.01) |
| *G01N 33/74* | (2006.01) |
| *G01N 30/88* | (2006.01) |
| *G01N 30/02* | (2006.01) |

(52) U.S. Cl.
CPC ............. *G01N 30/06* (2013.01); *G01N 30/74* (2013.01); *G01N 30/8665* (2013.01); *G01N 30/8675* (2013.01); *G01N 2030/027* (2013.01)

(58) Field of Classification Search
CPC .. G01N 30/8665; G01N 33/743; G01N 30/88; G01N 30/8675; G01N 30/06; G01N 30/74
USPC ..................................... 436/13, 71, 139, 161
See application file for complete search history.

(56) References Cited

U.S. PATENT DOCUMENTS

| | | | | |
|---|---|---|---|---|
| 5,516,528 | A * | 5/1996 | Hughes | A61K 31/565 424/423 |
| 2005/0222248 | A1* | 10/2005 | Joannou | C07C 45/673 514/456 |
| 2009/0209655 | A1* | 8/2009 | Joannou | A23L 33/105 514/685 |

OTHER PUBLICATIONS

Joannou, G. E. et al, Journal of Steroid Biochemistry and Molecular Biology 1995, 54, 167-184.*
Franke, A. A. et al, Clinical Chemistry 1996, 42, 955-964.*
Franke, A. A. et al, Proceedings of the Society for Experimental Biology and Medicine 1998, 217, 263-273.*
Gamache, P. H. et al, Proceedings of the Society for Experimental Biology and Medicine 1998, 217, 274-280.*
Zhang, Y. et al, Journal of Nutrition 1999, 129, 957-962.*
Franke, A. A. et al, Journal of Chromatography B 2002, 777,) 45-59.*
Maubach, J. et al, Journal of Chromatography B 2003, 784, 137-144.*
Grace, P. B. et al, Cancer Epidemiology, Biomarkers & Prevention 2004, 13, 698-708.*
Zhao, J. H. et al, Phytomedicine 2006, 13, 304-309.*
Wang, J. et al, Chinese Journal of Analytical Chemistry 2006, 34, 569-572.*
Grace, P. B. et al, Journal of Chromatography B 2007, 853, 138-146.*
Moors, S. et al, Molecular Nutrition & Food Research 2007, 51, 787-798.*
Yu, J. et al, Journal of Pharmaceutical and Biomedical Analysis 2009, 50, 939-946.*
Kunisue, T. et al, Jurnal of Agricultural and Food Chemistry 2010, 58, 9838-9846.*
Redruello, B. et al, Journal of Chromatography B 2015, 1005, 1-8.*

* cited by examiner

*Primary Examiner* — Arlen Soderquist

(74) *Attorney, Agent, or Firm* — Denise L. Mayfield; Dykema, Gossett PLLC

(57) ABSTRACT

Presented are improved and more sensitive methods for measuring levels of phytoestrogens in a biological sample, and specifically in a human urine sample, employing a High Pressure Liquid Chromatography method, coupled with a photodiode array analysis detection system. Calibration curve preparation for each of a panel of phytoestrogen analytes, including daidzein, equol and genistein, are provided employing techniques that demonstrate greater accuracy and sensitivity of sample level measurement. Clinically applicable techniques suitable for large population scale screening, diet and gut microflora characterization and disease analysis and correlation in human populations, such as in at risk breast cancer populations, through monitoring of phytoestrogen levels, is disclosed.

5 Claims, 1 Drawing Sheet

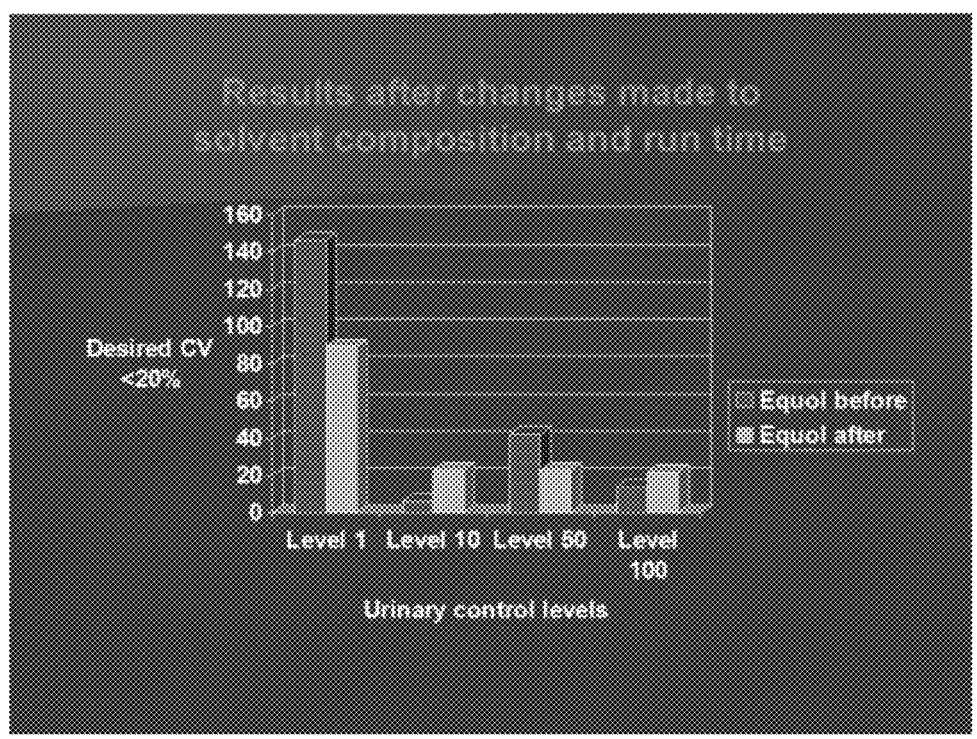

HPLC-PDA METHOD AND USES THEREOF IN PHYTOESTROGEN MEASUREMENT

GOVERNMENT SUPPORT

This invention was made with government support under DAMD 17-03-1-0274 awarded by the United States Department of Defense, U.S. Army Medical Research and Material Command. The government has certain rights in the invention.

BACKGROUND

Phytoestrogens are naturally occurring biologically active molecules that are observable in a majority of human fluids. These materials are derived from the diet and are believed to have many beneficial properties, particularly in relation to chronic degenerative diseases, including coronary heart diseases and cancer. It is generally accepted that the glucoside forms ingested with foods are hydrolyzed and the free aglycons are then converted to sulfate and glucuronide conjugates by the liver and other epithelial surfaces. These biological conjugates circulate in the plasma and are secreted in the urine and feces. Most researchers continue to measure hydrolyzed aglycons due to technical challenges of performing conjugate analysis. (Clark et al., 2002).

Many analytical methods for detection and quantitation of phytoestrogens and their metabolites in plants, plant derived products and biological matrices have been reported. When classified upon separation methodology, the analytical methods can be categorized into chromatographic and non-chromatographic techniques (Wu et al. 2004). High performance liquid chromatography (HPLC) coupled with various detection techniques including ultraviolet absorption (UV) are methods within the chromatographic category.

HPLC separation of phytoestrogens is generally carried out on reversed-phase (RP) columns with a mobile phase of methanol (MeOH) or acetonitrile (CH3CN, CN) and water containing a small amount of acid as a modifier. The structure of phytoestrogens and their metabolites mostly contains phenolic hydroxyl groups which exhibit a weak acidic nature. Thus applications of acidic modifiers such as formic acid (HCOOH), acidic acid (AcOH), trifluoroacetic acid (TFA) and phosphoric acid (H3PO4) can make the analytes easily disassociated in a solvent system, thus enhancing the chromatographic separation, resolution, and improvement of peak shape (Wu, et al. 2004).

The most commonly used coupling with HPLC has been UV detection. The primary advantage of HPLC over other methods such as gas chromatography (GC) is the ease of utilization and simple sample preparation procedures. It is also more robust than GC-based methods (Clarke et al., 2002). And although HPLC-UV is less specific than GC-MS, more than one analyte can be tested per assay (Wilkinson et al, 2002).

Ultraviolet detection, however, is non-specific, and cannot achieve good enough sensitivity (Wu et al.,). Also HPLC separation has poorer chromatographic resolution. (Wu et al., 2004). Mass spectrometries (GC-MS and LC-MS) are needed to achieve the sensitivity and selectivity needed when working at the lower levels encountered in biological matrices (Clark et al., 2003).

A need continues to exist in the medical arts for methods capable of measuring low levels of specific phytoestrogens in a biological sample. Such methods would provide techniques useful in the early detection of disease in a patient. The accurate measurement of phytoestrogens in a patient sample may be developed to provide new and novel methods for detecting breast cancer and other cancers in a patient. In particular, phytoestrogens may hold promise as potential markers for breast cancer disease where sufficiently population accessible and sensitive techniques are developed and studied to identify correlations between patient levels of these materials and risk of disease. However, currently available techniques limit these efforts. Improved methods having greater sensitivity measurement levels and improved laboratory techniques are needed to (1) correlate particular and informative compound metabolites with higher risk disease states and (2) create practical clinical protocols that may be used to accurately screen, assess and identify disease states in higher risk patient populations.

SUMMARY

In a general and overall sense, the present invention relates to methods for measuring phytoestrogens in a biological sample. In particular embodiments, the biological sample is a urine sample. In particular embodiments, the phytoestrogens comprise daidzein, equol and genistein.

In yet another aspect, the invention provides a method for assessing risk of a patient for breast cancer, the method comprising assessing relative risk of breast cancer by a patient's levels of a panel of phytoestrogens compared to a reference level of the panel of phytoestrogens in a control sample (control population).

In particular embodiments, a panel of three different phytoestrogens are measured in a urine sample obtained from a patient, particularly using a technique known as High Performance Liquid Chromatography (HPLC).

In another aspect, an improved and modified High Performance Liquid Chromatography (HPLC) method is provided. An improvement of the method is in an improved standard curve of each of several, particularly three, phytoestrogens. A significant improvement in accuracy and sensitivity is provided with the specifically defined phytoestrogen standard curves created, compared to conventional HPLC systems that employ a single standard serial dilution technique.

In particular embodiments, the panel of phytoestrogens measured comprise daidzein, genistein and equol.

In some aspects, the method comprises measuring phytoestrogen levels in a biological sample, said method comprising the steps of processing a biological sample, said biological sample comprising urine, comprising centrifuging the urine sample for about 10 minutes at about 3200 g and collecting the supenatant; combining a volume of the supernatant with a volume of sodium acetate buffer (pH 5.0) and β-glucuronidase/arylsulphatase to provide a mixture, and incubating the mixture for about hours at about 55° C., extracting the incubated sample with about 90 µl of an internal standard and about 7 ml ethyl acetate, removing the ethyl acetate under a nitrogen stream at about 55° C., redissolving the sample in about 0.05% formic acid and combining the sample with methanol to provide a redissolved biological sample, preparing a calibration curve for three phytoestrogens, wherein said three phytoestrogens are daidzein, genistein and equol, wherein the each calibration curve comprises 9 concentration points between 0.125 to 100.0 µmol/l, wherein each calibration curve is prepared using a serial dilution of a 100 µmol/l standard solution of each of the phytoestrogens daidzein, equol and genistein; and determining a level of daidzein, equol and genistein in the biological sample by high pressure liquid chromatography analysis, wherein a stock solution of 100 µmol/l of daidzein, equol or genistein is used to create a standard solution from which the calibration curve for the respective phytoestrogen is prepared, and wherein a quality control urine sample is employed as a control in the determination step, said quality control urine sample being provided at calibrated concentration points of 1, 10 and 100 µmol/l.

In some aspects of the method, the high performance liquid chromatography is coupled with photodiode array analysis.

In yet another aspect, a method for providing a patient's phytoestrogen profile level is provided, the panel of phytoestrogens comprising daidzein, equol and genistein. In some embodiments, a patient's phytoestrogen profile may be used as an indicator to correlate the patient's relative risk for a disease, so as to serve as a disease assessment tool and/or indicator.

By way of example, the patients phytoestrogen panel profile levels may be correlated with the patient's risk assessment for breast cancer As used herein, reference to "not" a value or parameter generally means and describes "other than" a value or parameter. For example, the method is not used to treat cancer of type X means the method is used to treat cancer of types other than X.

As used herein and in the appended claims, the singular forms "a," "or," and "the" include plural referents unless the context clearly dictates otherwise.

These and other aspects and advantages of the present invention will become apparent from the subsequent detailed description and the appended claims. It is to be understood that one, some, or all of the properties of the various embodiments described herein may be combined to form other embodiments of the present invention.

BRIEF DESCRIPTION OF THE DRAWINGS

FIG. 1 Results after changes made to solvent composition and run time.

DETAILED DESCRIPTION OF THE PREFERRED EMBODIMENTS

Terms are used herein as generally used in the art, unless otherwise defined as follows.

The following examples present a description of various specific aspects of the intended invention, and are not presented to limit the intended invention in any way.

Example 1—Materials and Methods

The present example presents the materials and methods that may be used in the practice of the present invention.

Instrumentation

AH samples were analyzed using a Waters 2695 Separations HPLC module equipped with a 2996 photodiode array detector (Waters, Millford, Mass., USA), Chromatographic processing was done using the Waters Empower1 M1 Software. The reversed-phase silica column was an XTERNI® MS CIS 3.5 pin, 4.6×250 mm (Waters). Analyses were carried out tinder isocratic conditions with a solvent, mixture consisting of 1% solvent R (acetonitrile) and 39% solvent C (methanol) in solvent A (0.1% formic acid in water). The flow-rate was 1.5 ml/min, the column temperature was 40° C., and the run time was set to 35 min, The injection volume was 30 µl and all samples were analyzed in duplicate, Ultraviolet detection was done at a wavelength which corresponded to each analyzes maximum absorption, 249 nm for daidzein, 230 nm for equol, and 260 nm for genistein. The internal standard (4-HBPH) was detected simultaneously with and at the same wavelength as described above for each compound.

Chemicals

Daidzein (98%), (+\−) Equol, and Genistein (99%) were purchased from Indofine Chemical Co. (Hillsborough, N.J.), methyl sulfoxide 99.9%, ethyl acetate 99.9%, formic acid 99%, lyophilized urine control material, HPLC-grade methanol; HPLC-grade acetonitrile, and HPLC-grade water were purchased from Fisher Scientific (Houston, Tex.). B-gueuronidase (*Helix pomatia*, HP-2S) and 4-hydroxybenzophenone (4-HB.PH), acetic acid 99.8%, and sodium acetate anhydrous were obtained front Sigma-Aldrich (Saint Louis, Mo.)

Standard Solutions

Standard stock solutions were prepared by dissolving 5 mg of each analyte in DMSO in 40 ml of methanol. Working standard solutions were prepared by serial dilutions of the stock solutions in mobile phase to cover tire linear range of the analytes (0.781 to 100 µmol/l) which is known, to be found in human urine.

Quality Control Samples

Quality control (QC) samples were prepared by using commercially available lyophilized human urine as the matrix which was analyzed and found to be free of any detectable levels of the phytoestrogens being analyzed. Two quality control (QC) samples were thus prepared by spiking the urine with, phytoestrogen standards in low and high concentrations within the calibration range. A set of low and high controls was analyzed with every batch of 25 samples.

Collection of Sample

A urine sample was collected in a sterile urine container, and approximately 5 ml was aliquoted in a cryogenic vial and kept at −80 'V until it is ready to be processed and analyzed. The participants were informed to collect the first morning void and preferably urine that had been held in the bladder overnight.

Preparation of Samples

For each sample, 2 ml of urine was added to 7 ml sodium acetate buffer (pH 5.0) and 30 pi (J-glucuronidase/arylsulphatase). The samples were vortexed and incubated for 3 h at 37° C., followed by extraction with 90 pi internal standard (8 mg 4-HBPH in 100 ml ethyl acetate) and 7 ml ethyl acetate at 55° C. The solvent was removed under a gentle stream of nitrogen using the Pierce Reacti-vap Evaporator (Rockford, Ill.) at. 55° C. and lite samples were redissolved in 0.05% formic acid in water-methanol 50/50 (v/v) followed by analysis.

Calibration Curves

Each calibration standard was assayed in duplicate and the standard curves were fitted using a linear through zero-calibration curve. Quantification was done by measuring peak areas based on calibration plots of the peak areas of each of the standards and corrected for losses by using internal standard in calculating unknown concentrations.

Inter-assay coefficients of variation were determined by observing results of each control level across 5 different days, Intra-assay precision was determined by analyzing each control level 10 times. The level of acceptance for precision was set at 20% (Maubach). Both intra- and inter-assay CV were at or below 20%.

Example 2—Measurement of Phytoestrogens in Human Urine

The present example presents the method by which phytoestrogens may be measured in a human urine sample.

A method for the purpose of extracting the isoflavones daidzein, equol, and genistein from human urine using HPLC-PDA (also known as photodiode array, UV, DAD) is demonstrated here. The method based on the method developed by Maubach, et al., that involves less processing steps and shorter incubation times than previous published methods, with a stated recovery of 100% (+/−14%) in human serum and urine, is provided.

This example examined samples from 1500 human participants with an equal number of diagnostic, high risk, and control cases. The data gathered will include a food questionnaire and blood samples for the determination of serum levels of insulin, glucose, SHBG, IGF-1, IGF-BP3, estradiol, and estrone by ELISA. These tests are also performed. The study is aimed at finding a correlation between dietary practices and the low incidence of breast cancer in this population.

Collection of Sample

A urine sample will be collected along with the blood sample in a sterile urine container, and approximately 5 ml will be aliquoted in a cryogenic vial, and kept at −80° C. until it is ready to be processed and analyzed.

Since the participants are drawn fasting, the urine will be taken at this time, and the participants have been informed to collect the first morning void and preferably urine that has been held in the bladder overnight.

Sample Size

When an equal number of control, high risk, and diagnostic case samples with similar characteristics totaling 39 are collected, a series of laboratory tests on serum for this group is performed. This sample size is equal to the total number of available wells in the ELISA test method in which testing is done in duplicate.

The sample size for the urine testing will be up to 120. Although there are a total number of 27 wells available in the dry bath, batches of samples can be processed and added onto the separations module to fit its capacity which is 120. Therefore, 9 standards (do not require incubation), 9 controls, and 24 unknowns will be analyzed in one chromatographic run.

Materials and Methods:

Instrumentation

All samples will be analyzed using a Waters 2695 Separations HPLC module equipped with a 2996 photodiode array detector (Waters, Millford, Mass., USA). Chromatographic processing will be done using the Waters Empower™ 2 Software. The reversed-phase silica column is an XTERRA® MS C18 3.5 pm, 4.6×250 mm (Waters).

Analysis will be carried out under isocratic conditions with an eluent mixture consisting of 46% solvent B (acetonitrile-methanol 20/80 (v/v)) in solvent A (0.05% formic acid in water). The flow-rate will be 1.5 ml/min, the column temperature will be 40° C., and the run time will be set to 20 min, sufficient for all compounds to elute. The injection volume will be 30 pl and all samples will be analyzed in duplicate. Ultraviolet detection will be done at a wavelength corresponding to the most intense absorption maximum of each analyte, i.e. 249 nm for daidzein, 230 nm for equol, and 261 nm for genistein. The internal standard (4-HBPH) will be detected simultaneously with and at the same wavelength as described above for each compound.

Chemicals

Daidzein (98%), (+/−) -Equol, Genistein (99%) Indofine Chemical Co., methyl sulfoxide 99.9%, sodium acetate 5.0 pH, ethyl acetate 99.9%, formic acid 99%, HPLC grade methanol, acetonitrile, and water were purchased from Fisher Scientific (Houston, Tex.). 11-glucuronidase (Helix pomatia, HP-2S) and 4-hydroxybenzophenone (4-HBPH), acetic acid 99.8%, and sodium acetate anhydrous were obtained from Sigma-Aldrich, Saint Louis, Mo.

Preparation of Samples

Once the urine is thawed, it is centrifuged for 10 minutes at 3200 g using the Graham-Field Economy Electric Centrifuge. 2 ml are added to 7 ml sodium acetate buffer (pH 5.0) and 30 μ β-glucuronidase/arylsulphatase. The samples are vortex-mixed and incubated for 3 h at 37° C., followed by extraction with 90 μ internal standard (8 mg 4-HBPH in 100 ml ethyl acetate) and 7 ml ethyl acetate. The solvent is removed under a gentle stream of nitrogen using the Pierce Reacti-Vap Evaporator at 37° C. [1] and the sample is redissolved in 150 μ 0.05% formic acid in water-methanol 50/50 (v/v) prior to analysis.

Calibration curves, recoveries, repeatability, limits of detection and quantitation Stock solutions are prepared by taking 5 mg of the pure analyte and dissolving in (0.5 ml) DMSO followed by the addition of methanol (40 ml). Working standard solutions containing individual analytes are prepared by serially diluting stock solutions in mobile phase to obtain a set of calibration standards covering the expected range in the urine matrix (0.195 to 100.00 μmol/l for daidzein, 0.098 to 100.00 μmol/l for equal, and 0.391 to 100.0 μmol/l) for each analyte. Each calibration standard will be assayed in duplicate (Thomas, et al.) and standard curves are fitted by first order linear regression. The peak areas versus the nominal concentrations will be used to generate the calibration curves and the concentrations of the analytes in urine will be determined from these curves.

Quality control (QC) specimens will be prepared by spiking the urine of a subject in whom these compounds are not detectable with 1, 10 and 100 μmol/l concentrations of phytoestrogen standards. These three levels of controls for each analyte will be run in duplicate. Acceptance of an analytical run will be dependent upon four of the six controls passing a level of acceptance of 20% (with the additional acceptance criteria that the two failing controls could not be at the same concentration level). QC samples may be stored as aliquots −80° C. until use. (Maubach, et al., Thomas, et al. Valentin-Blasini, et al.)

For the determination of recoveries, daidzein, equal, and gen stein at 1, 10, and 100 μmol/l in methanol (n=5) will be spiked into commercially prepared urine. (Maubach, et al., Valentin-Blasini, et al.).

Both the intra- and inter-assay variations in measurements will be determined on the urine samples containing daidzein, equol, and genistein (n=5). The level of acceptance for precision will be set at 20%. The limit of detection (LOD) will be defined as the analyte concentration that gives a signal-to-noise (S/N) ratio of 3. The limit of quantitation (LOQ) referred to the lowest concentration of analyte (n=5) that could be determined with 20% accuracy and precision. (Maubach, et al.)

Stock Solutions

Analytes were Dissolved in DMSO.

Standards

Apers, et al. prepared 6 concentration levels and injected them twice. The 6 samples covered the range of the method. For each level a SD and CV were calculated. Cochran's test was used to check for variations at different concentrations. The results obtained on the 6 levels were analyzed by ANOVA single factor to see if significantly different. Within and between level variation coefficients were calculated RSD between-days is <5%; Ccalc<Ccrit; the variation of the method can be considered equal for concentration level within this range.

Valentin-Blasini, et al. prepared calibration curves daily from fresh aliquots of nine standards spiked with internal standards. These standard mixtures were injected twice (before and after analysis of the unknowns) to insure that the calibration curve was accurate for all unknowns analyzed on any given day.

Quality Control

Thomas, et al. prepared QC solutions independently from calibration standards in low, mid and high concentrations.

Assessing Linearity

Apers, et al. assessed linearity using the least squares line and calculating correlation coefficients. Calibration curves obtained were tested on the slope (a≠0) and intercept (b=0) by means of Student's t-tests. LOF (lack of fit) test and residuals graphically were examined. (Apers, et al.)

To determine linearity and range, Thomas, et al. assayed each calibration standard in duplicate. The standard curves were then fitted by least squares linear regression analysis using a 1/x weighting.

Valentin-Blasini, et al. states that analyte and internal standard peak areas were integrated and the ratio of analyte to internal standard plotted against known analyte concentration. These plots were weighted so that each point in the curve contributed equally to a best-fit line. The resulting slope and y-intercept values for each analyte were used to interpolate analyte values in unknown specimens.

Precision

Repeatability and the inter-day intermediate precision were determined by analyzing 6 samples on 3 different days. SD and CV were calculated for each day. Results were analyzed by ANOVA single factor. Within and between days variation coefficients were calculated as well. (Apers, et al.).

Nurmi, et al.'s intra-assay precision was determined by analyzing each control ten times. Inter-assay precision was determined with results obtained on different days. The system was calibrated during each analysis assay.

Thomas, et al. prepared quality control samples in quintuplicate for determination of assay accuracy, precision, and limit of quantitation. The level of acceptance was set at 20% for both accuracy and precision at all levels of the control samples, including the limit of quantitation. LOQ was n=5. During analysis of a sample set, three levels of controls were run in duplicate. Acceptance of an analytical run was then dependent upon four of the six controls passing the 20% cut-off (with the additional acceptance criteria that the two failing controls could not be at the same concentration level).

Yamamoto, et al. conducted intra-and inter-assay assessments by repeated analysis of three urine samples of three different concentrations. The CVs were <10% in the three samples.

Recovery

Maubach, et al. stated that "recoveries, after spiking with daidzein, equol, and genistein in concentrations of 1, 10 and 100 µmol/l (n=5 for all measurements) were found to be . . . 100% (+1-14.1%) in urine and serum."

Thomas, et al. used three control levels of analyte at high mid and low levels of the calibration rate. Each control was prepared with an n of 10. The controls peak heights were compared to "recovery standards" which were formulated in the HPLC mobile phase in order to provide an estimate of the extraction recovery.

Valentin-Blasini, et al. calculated urinary recovery rates based on 100 ng of each standard spiked into phytoestrogen-free synthetic urine.

Reporting

Analytes below the lowest standard were reported as non-detects (Valentin-Blasini, et al.).

These studies have shown that HPLC coupled with photodiode array along with improved resolution and sensitivity of instrumentation as well as the continuing development of new analytical techniques and refinements to existing techniques makes this method useful in the laboratory.

TABLE 1

Preparation of 0.05% formic acid in water (v/v) - Solvent A

For the preparation of 500 ml of 0.05% formic acid
in water Formic acid sold in 1LL at 99%
$V_1 = 500$ ml
$C_1 = 0.05\%$
$V_2 = x$
$C_2 = 99\%$
$(500)(0.05) = (99)(x)$
$x = 0.25$ ml
$x = 250$ µl formic acid
Therefore, 250µ. formic acid + 500 ml
water = 500 ml of 0.05% formic acid.

For redissolving Samples After Drying By Nitrogen

For redissolving samples after drying by nitrogen, the mixture is 0.05% formic acid in water/methanol 50/50. Therefore, you would take the above mixture of 0.05% formic acid and combine it with methanol 50/50.

TABLE 2

Preparation of 500 µmol/l stock solutions

Preparation of 500 µmol/l stock solutions (all soluble in DMSO and methanol):
MW Daidzein = 254.2
MW Equol = 242.27
MW Genistein = 270.2

$$?\text{mg } D = \frac{500 \ \mu\text{mol}}{L} \ 40 \text{ml} \times \frac{1 \text{ L}}{1000 \text{ ml}} \times \frac{1 \times 10^{\wedge}6 \text{ mole}}{1 \ \mu\text{mol}} \times \frac{254. \text{ g}}{1 \text{ mole}} \times \frac{1000 \text{ mg}}{1 \text{ g}} = 5.084 = 5.0 \text{ mg } D$$

$$?\text{mg } E = \frac{500 \ \mu\text{mol}}{L} \ 40 \text{ ml} \times \frac{1 \text{ L}}{1000 \text{ ml}} \times \frac{1 \times 10^{\wedge}6 \text{ mole}}{\mu\text{mol}} \times \frac{247.27 \text{ g}}{1 \text{ mole}} \times \frac{1000 \text{ mg}}{1 \text{ g}} = 4.945 \text{ mg } E = 5.0 \text{ mg } E$$

$$?\text{mg } G = \frac{500 \ \mu\text{mol}}{L} \ 40 \text{ ml} \times \frac{1 \text{ L}}{1000 \text{ ml}} \times \frac{1 \times 10^{\wedge}6 \text{ mole}}{\mu\text{mol}} \times \frac{270.2 \text{ g}}{1 \text{ mole}} \times \frac{1000 \text{ mg}}{1 \text{ g}} = 5.404 \text{ mg } G = 5.0 \text{ mg } G$$

Desired concentration:   100 µmol/l = 1 dilution factor

TABLE 2-continued

Preparation of 500 µmol/l stock solutions

Stock solution: 500 µmol/l    5

$$50 \text{ ml needed} \times \frac{1}{5} = \frac{50}{5} = 10 \text{ ml stock standard}$$

Therefore:
50 ml stock solution = to 10 ml stock standard + 40 ml diluent (methanol) = 100 µmol/l standard solution.

TABLE 3

Serial dilutions of 100 µmol/l standard solution:

| Tube No. | 1 | 2 | 3 | 4 | 5 | 6 | 7 | 8 | 9 |
|---|---|---|---|---|---|---|---|---|---|
| Volume | 2 ml | 2 ml of Tube 1 | 2 ml of Tube 2 | 2 ml of Tube 3 | 2 ml of Tube 4 | 2 ml of Tube 5 | 2 ml of Tube 6 | 2 ml of Tube 7 | 2 ml of Tube 8 |
| Conc. Or Solvent | 100 µmol/l solution | 2 ml meth | 2 ml meth | 2 ml meth | 2 ml meth | 2 ml meth | 2 ml meth | 2 ml meth | 2 ml meth |
| Dilution factor | 1:5 | 2:4 | 2:4 | 2:4 | 2:4 | 2:4 | 2:4 | 2:4 | 2:4 |
| Final dilution | 1/5 | 1/10 | 1/20 | 1/40 | 1/80 | 1/160 | 1/320 | 1/640 | 1/1280 |

TABLE 4

Preparation of 500 µmon stock solutions
Serial dilutions of 100 µmon standard solution:

| Tube No. | 10 | 11 | 12 | 13 | 14 |
|---|---|---|---|---|---|
| Volume | 2 ml of Tube 9 | 2 ml of Tube 10 | 2 ml of Tube 11 | 2 ml of Tube 12 | 2 ml of Tube 13 |
| Conc. Or Solvent | 2 ml meth | 2 ml meth | 2 ml meth | 2 ml meth | 2 ml meth |
| Dilution factor | 2:4 | 2:4 | 2:4 | 2:4 | 2:4 |
| Final dilution | 1/2560 | 1/5120 | 1/10240 | 1/20480 | 1/40960 |

TABLE 5

Preparation of 500 µmol/l stock solutions
Desired range is 0.012-100.0 µmol/l
Actual concentrations:

| Tube | Final Dilution | Equation | Concentration (µmol/l) |
|---|---|---|---|
| 1 | 1/5 | 500 µmol/l × 1/5 | 100 |
| 2 | 1/10 | 500 µmol/l × 1/10 | 50 |
| 3 | 1/20 | 500 µmol/l × 1/20 | 25 |
| 4 | 1/40 | 500 µmol/l × 1/40 | 12.5 |
| 5 | 1/80 | 500 µmol/l × 1/80 | 6.25 |
| 6 | 1/160 | 500 µmol/l × 1/160 | 3.125 |
| 7 | 1/320 | 500 µmol/l × 1/320 | 1.563 |
| 8 | 1/640 | 500 µmol/l × 1/640 | 0.781 |
| 9 | 1/1280 | 500 µmol/l × 1/1280 | 0.391 |
| 10 | 1/2560 | 500 µmol/l × 1/2560 | 0.195 |
| 11 | 1/5120 | 500 µmol/l × 1/5120 | 0.098 |
| 12 | 1/10240 | 500 µmol/l × 1/10240 | 0.049 |
| 13 | 1/20480 | 500 µmol/l × 1/20480 | 0.024 |
| 14 | 1/40960 | 500 µmol/l × 1/40960 | 0.012 |

Range of 0.125 µmol/l to 100.00 µmol/l taken from Maubach; however, in Valentin-Blasini, et al.'s study (N=199), samples taken from a nonrepresentative subset of adults who participated in the study with a race/ethnicity of non-Hispanic white 29%, non-Hispanic black 43%, Mexican American 23%, and other 5%, the linear ranges for the calibration curve parameters were as follows:
Daidzein 0.039-47.20 µmol/l
Equol 0.247-41.27 µmol/l
Genistein 0.029-74.02 µmol/l
(units converted from µg/ml).

This means recovered for daidzein, equol, and genistein were 317, 36, and 129 ng/ml, respectively, (1.24, 0.148, and 0.477 µmol/l). These ranges are within the range used by Maubach, et al.

TABLE 6

Standards to be used

| Standard No. | Tube | Concentration (µmol/l) |
|---|---|---|
| 10 | 1 | 100 |
| 9 | 2 | 50 |
| 8 | 3 | 25 |
| 7 | 4 | 12.5 |
| 6 | 7 | 1.563 |
| 5 | 9 | 0.391 |
| 4 | 10 | 0.195 |
| 3 | 12 | 0.049 |
| 2 | 14 | 0.012 |
| 1 | 15 | Blank |

TABLE 7

Preparation of quality control samples in commercially prepared urine
To make three different concentrations, the following ml amounts of a 10 µmol/l stock solution is added to 2 ml of urine:
Vl = ml urine (volume required); C1 = molar concentration required which is 1, 10 or 100 µmol/l; V2 = unknown volume of stock solution needed to add to urine to make the desired concentration; C2 = concentration of stock solution.

| 1 µmol/l | 10 µmol/l | 100 µmol/l |
|---|---|---|
| V1 = 2 ml | V1 = 2 ml | V1 = 2 ml |
| C1 = 1 µmol | C1 = 10 µmol/l | C1 = 100 µmol |
| V2 = x ml | V2 = x ml | V2 = x ml |

TABLE 7-continued

Preparation of quality control samples in commercially prepared urine
To make three different concentrations, the following ml amounts of a 10
µmol/l stock solution is added to 2 ml of urine:
VI = ml urine (volume required); C1 = molar concentration required
which is 1, 10 or 100 µmol/l; V2 = unknown volume of stock solution
needed to add to urine to make the desired concentration; C2 =
concentration of stock solution.

| 1 µmol/l | 10 µmol/l | 100 µmol/l |
|---|---|---|
| C2 = 100 µmol/l | C2 = 100 µmol/l | C2 = 100 µmol/l |
| (2)(1) = (100)(x) | (2)(10) = (100)(x) | (2)(100) = (100)(x) |
| x = 0.02 ml | x = 0.2 ml | x = 2.0 ml |
| x = 20 µl | x = 200 µl | x = 2000 µl |

TABLE 8

First Modification - Changes in the preparation of standard solutions
from a single standard solution to separate standard solutions
reduced interference and demonstrated better recovery.

| | Recovery Before Changes in 100 µmol/l | Recovery After Changes in 100 µmol/l | CV Before <20 desirable | CV After <20% desirable |
|---|---|---|---|---|
| Daidzein | 54.508 | 99.892 | 41.53888 | 0.076409 |
| Equol | 50.865 | 98.826 | 46.05931 | 0.835045 |
| Genistein | 53.968 | 98.705 | 42.28091 | 0.921671 |

Reference method not clear
Analytes showed interference in absorbance at all levels when mixed in standard solution
Separated for better recovery

TABLE 9

Second Modification
Changes in the incubation and drying step from 37° C. to 55° C.

| | Urine controls 100 µmol/L | |
|---|---|---|
| Analyte | Before | After |
| Daidzein | 0.00 | 40.49877 |
| Equol | 0.00 | 23.22859 |
| Genistein | 0.00 | 62.19 |

TABLE 10

Third Modification
Changes in the formulation of the preparation or urine controls

| | Urine controls 100 µmol/L | |
|---|---|---|
| Analyte | Before | After |
| Daidzein | 40.4987 | 74.0776 |
| Equol | 23.2285 | 86.3836 |
| Genistein | 62.1900 | 88.3523 |

TABLE 11

Fourth Modification Changes in solvent composition and run time

| | |
|---|---|
| 1. | Changed solvent A to 0.1% formic acid in water. |
| 2. | Changed solvent B to 1% CAN and 39% MeOH. |
| 3. | Extended run time to 35 minutes. |

Prophetic Example 3—Correlation of Phytoestrogen Levels in Urine with Risk Assessment for Breast Cancer While outcomes will vary depending on the particular parameters of a subject, (diet, cancer predisposition and diagnosis, gut microbiota population, etc.), phytoestrogen consumption by participants in the three categories will be examined (normal, at risk, and with breast cancer) and any associations will be assessed. "Normal" levels pf phytoestrogens depend on what is consumed by the subject as well as what phytoestrogens are being manufactured by gut microbiota from diet. There are studies which show conflicting results (See Grace et al. (2004), Cancer Epidemiol Biomarkers Prey, 13 (5): 699-708; Taylor et al, (2009), Nutrition Reviews, 67(7): 398-415). Other factors have been reported to contribute to the prevention of cancer in reproductive organs or contribute to cancer risk in some cases, in combination with phytoestrogens. These other factors include, for example, the subjects' history or presence of cancer and/or the subjects' consumption of high levels of phytoestrogens that result in an estrogenic effect.

This prophetic example and a future course in these studies will examine the normal microbiota and its relationship with phytoestrogens and potential correlation and inhibition and/or prevention of cancer in at risk populations. The gut microbiota is a topic of great interest at this time. The role that the gut microbiota contributes to the development and progression of cancer, particularly in women, and regimes for potentially modifying a subject's gut microflora population through phytoestrogen level monitoring and manipulation of same through diet and gut microflora assessment, will be developed. Methods for improving a subjects overall health and wellbeing through gut microflora population optimization via diet induced phytoestrogen balance will also be devised.

BIBLIOGRAPHY

The following references are incorporated herein in their entirety.

Apers, S., Naessens, T., Van Den Steen, K., Cuyckens, P., Clayes, M., Pieters, L., Vlietnick, A. Fast high-performance liquid chromatography method for quality control of soy extracts. J. Chromatogr. A 1038 (2004) 107-112.

Clarke, D. B., Lloyd, A. S., Botting, N. P., Oldfield, M. F., Needs, P. W., Wiseman, H, Measurement of intact sulfate and glucuronide phytoestrogen conjugates in human urine using isotope dilution liquid chromatography-tandem mass spectrometry with [13Cj] isoflavone internal standards. Analytical Biochemistry 309 (2002) 158-173, Franke. A. A. Custer, L. J., Wang, W, Shi. C, Y. HPLC analysis of isoflavonoids and other phenolic agents from foods and from human fluids. Proc. Soc. Exp. Biol. Med. 1998: 217: 263273.

Horwitz, W. Evaluation of analytical methods used for regulation of foods and dregs. Analytical Chemistry, 54 (1.982) 67A-76A.

Key, P. E., Finglas, P. M., Coldham, N., Batting, N., Oldfield, M, P., Wood, R. An international quality assurance scheme for the quantitation of daidzein and genistein in food, urine and plasma. Food Chemistry 96 (2006) 261-272.

Nurmi, T., Voutilaninen, S., Nyyssonen, K., Adlercreutz, H., Salonen, J. T. Liquid chromatography method for plant and mammalian lignans in human urine. J. Chromatogr, B 798 (2003) 101-110.

King, R, A. and Bursill, D, B, Plasma and urinary kinetics of the isoflavones daidzein and genistein after a single soy meal in humans. Am. J. Clin. Nutr, 1998; 67: 867-72.

Maubach, J,. Bracks, M. E., Heyerick, A., Depypere, H. T., Serreyn, R. F. Marcel, M. M. Da Keukeleire, D. D. Quantitation of soy-derived phytoestrogens in human breast tissue and biological fluids by high-performance liquid chromatography. J. Chromatogr. B 784 (2003) 137144.

Ungar, Y., Osundabunsi. P., Shimoni, E. Thermal stability of genistein and daidzein and its effect on their antioxidant activity, I, Agric. Food Chem. 2003. 51, 4394-4399.

Valentin Blasini, L., Blount, B. C. Caudill, S. P., Needham, L. L., Urinary and serum concentrations of seven phytoestrogens in a human reference population subset. Journal of Exposure Analysis and Environmental Epidemiology (2003) 13, 276-282.

Valentin-Blasini, Blount, B. C. Rogers, H, S., Needham, L. L. HPLC-MS/MS method for the measurement of seven phytoestrogens in human serum and urine, Journal of Exposure Analysis and Environmental Epidemiology (2000) 10, 799807.

Wilkinson, a. P., Wahalu, K., Williamson, G. Identification and quantification of polyphenol phytoestrogens in foods and human biological fluids. J. Chromotogr. B, 777 (2002) 93-109.

Wu, Q., Wang, M., Simon, J, E, Analytical methods to determine phytoestrogens compounds, J, Chromatogr. B. 81.2 (2004) 325-355.

Yamomoto, S., T, Sobue, T., Sasaki, S., Kobayashi, M., Aral, Y., Uehara, M. Adlercroutz, IL, Watanabe, S. Takashashi, T., Litoi, Y. Iwase, Y., Akabane, M. Tsugane, S, Validity and reproducibility of a self-administered food-frequency questionnaire to assess Isoflavone Intake in a Japanese population in comparison with dietary records and blood and urine isoflavones.

Zhang, Y., Wang, G-I., Song, T. T., Murphy, P. A. Stendrieh, S. Urinary disposition of the soybean isoflavones daidzein, genistein, and glycitcein differs among humans with moderate fecal isoflavone degradation activity. J, Nutr. 129 (1999) 957.

Zheng, W., Dai, Q., Custer, L, J., Shu, X-O., Wen, W-Q., Jin, P., Franke. A. A. Urinary excretion of isoflavonoids and the risk of breast cancer.

I claim:

1. A method for measuring phytoestrogen levels in a biological sample, said method comprising the steps of:

processing a biological sample, said biological sample comprising urine, comprising:
centrifuging the urine sample for about 10 minutes at about 3200 g and collecting the supernatant;
combining a volume of the supernatant with a volume of sodium acetate buffer (pH 5.0) and β-glucuronidase/arylsulphatase to provide a mixture, and incubating the mixture for about 3 hours at about 55° C.;
extracting the incubated sample with about 90 pl of an internal standard and about 7 ml ethyl acetate;
removing the ethyl acetate under a nitrogen stream at about 55° C.;
redissolving the sample in about 0.05% formic acid and combining the sample with methanol to provide a redissolved biological sample;
preparing a calibration curve for three phytoestrogens, wherein said three phytoestrogens are daidzein, genistein and equol, wherein the each calibration curve comprises 9 concentration points between 0.125 to 100.0 μmol/l, wherein each calibration curve is prepared using a serial dilution of a 100 μmol/l standard solution of each of the phytoestrogens daidzein, equol and genistein; and
determining a level of daidzein, equol and genistein in the biological sample by high pressure liquid chromatography analysis,
wherein a stock solution of 100 μmol/l of daidzein, equol or genistein is used to create a standard solution from which the calibration curve for the respective phytoestrogen is prepared, and wherein a quality control urine sample is employed as a control in the determination step, said quality control urine sample being provided at calibrated concentration points of 1, 10 and 100 μmol/l.

2. The method of claim 1 wherein high performance liquid chromatography analysis is coupled with photodiode array analysis.

3. The method of claim 1 wherein measuring the amount of phytoestrogen level of each of the daidzein, equol and genistein in the biological sample provides a patient phytoestrogen profile.

4. The method of claim 3 wherein the patient phytoestrogen profile may be used to correlate a patient's risk assessment for a disease.

5. The method of claim 4 wherein the patient's risk assessment is for breast cancer.

* * * * *